United States Patent [19]
Heijink

[11] Patent Number: 5,139,742
[45] Date of Patent: Aug. 18, 1992

[54] DISPOSABLE LIQUID TESTING DEVICE

[75] Inventor: Peter K. Heijink, Amersfoort, Netherlands

[73] Assignee: Livestock Control Holding B.V., MT Wijk bij Duurstede, Netherlands

[21] Appl. No.: 803,083

[22] Filed: Dec. 4, 1991

[30] Foreign Application Priority Data

Dec. 10, 1990 [NL] Netherlands ............ 9002708

[51] Int. Cl.⁵ .................... G01N 31/22; B01L 3/00
[52] U.S. Cl. ............................. 422/58; 422/102; 422/99; 422/68.1
[58] Field of Search ............ 422/102, 99, 68.1, 58, 422/74, 61

[56] References Cited

U.S. PATENT DOCUMENTS

| | | | |
|---|---|---|---|
| 4,042,337 | 8/1977 | Griffith | 422/102 |
| 4,859,603 | 8/1989 | Dole | 422/61 |
| 4,990,075 | 2/1991 | Wogoman | 422/61 |
| 5,069,878 | 12/1991 | Ehrenkrang | 422/58 |

Primary Examiner—James C. Housel
Assistant Examiner—Lien Tran
Attorney, Agent, or Firm—Peter L. Michaelson

[57] ABSTRACT

A disposable liquid testing device using essentially a cup-shaped container, wherein the container is provided with an outer cup to be sealingly placed and axially fixed on the bottom part of the container. The outer cup can be put in at least two coplanar end positions relative to the container. The bottom of the container is provided with at least one liquid passage and at least one reagent is applied on the side of the bottom facing the outer cup. The bottom of the outer cup has at least one reservoir which is in register with the liquid passage in one end position of the outer cup and in register with the reagent in the other end position.

16 Claims, 2 Drawing Sheets

DISPOSABLE LIQUID TESTING DEVICE

This invention relates to a disposable liquid testing device consisting essentially of a cup-shaped container.

In testing a liquid for the occurrence of a specific substance it is conventional to carry out a (bio)chemical test. For the test to be reliable, an accurate amount of a sample must be contacted with an accurate amount of reagent. Under laboratory conditions the required accuracy can be easily obtained, but under non-laboratory conditions or field conditions this is appreciably more difficult because of the non-availability of the required instruments or the insufficient skill on the part of their user.

The liquid testing systems employed in non-laboratory conditions generally utilize (test) tubes and/or paper strips provided with a specific reagent. The test is generally based on the observation of color differences. When tubes are used, the observation of color intensity differences between the edge of the tube and the center is difficult. When a paper strip is used, exact color observation is often impeded by the non-smooth surface of the paper strip.

The object of this invention is to provide a liquid testing instrument which combines great accuracy with great ease of operation while the required amount of reagent can be minimized. According to the invention this object is attained with a disposable testing device of the above type, in which the container is provided with an outer cup to be sealingly placed and axially fixed on the bottom part of the container, which outer cup can be put in at least two coplanar end positions relative to the container, the bottom of the container is provided with at least one liquid passage and at least one reagent is applied on the side of that bottom facing the outer cup, and the bottom of the outer cup comprises at least one reservoir which is in register with the liquid passage in one end position of the outer cup and in register with the reagent in the other end position.

By means of such a disposable device, e.g., a stockkeeper can very easily and accurately test fresh milk for the presence of progesterone, which substance indicates the fertility of the animal. For this purpose the container is filled with fresh milk, after which the outer cup is placed in such a position that the reservoir contained therein is filled with a closely determined amount of milk. By rotating or shifting the outer cup relatively to the container, the reservoir with the fresh milk is put in a position in which the milk can react with the closely determined amount of reagent applied to the bottom of the container during manufacture of the testing device, which reagent is adapted to the content of the reservoir arranged in the bottom of the outer cup. The color change occurring or not occurring after some time can be read with the eye through a sight glass which is arranged, e.g., in the bottom of the outer cup or in the bottom of the container.

Thus, the amounts of reagent and test liquid are always exactly adapted to each other and the performance of the test no longer requires any accuracy of the stock-keeper or the operator.

An embodiment of the testing device according to the invention is illustrated in the accompanying drawings in which FIG. 1 is a side view of the testing device;

Figure 1:
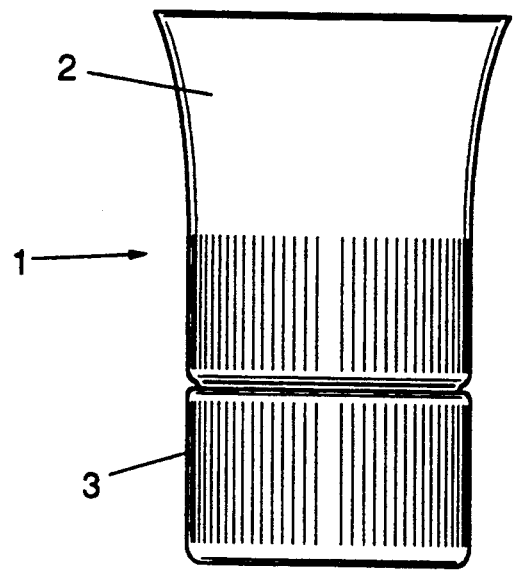
Figure 2:
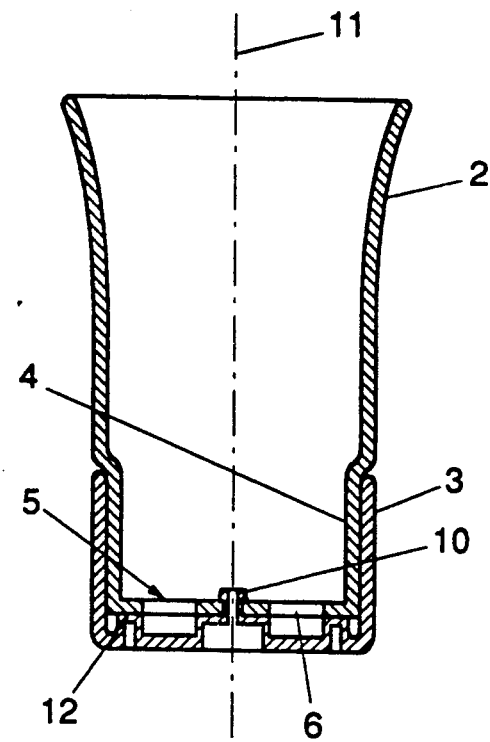
FIG. 2 is a longitudinal section of the testing device shown in FIG. 1.
Figure 3:
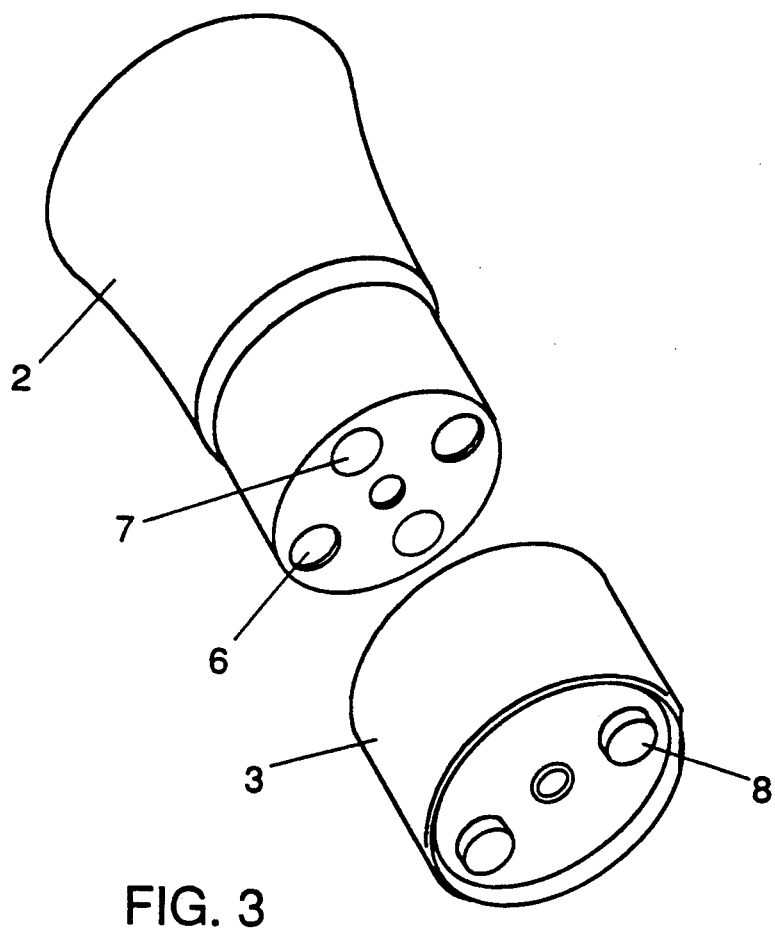
FIG. 3 shows the container and the outer cup of the testing device in separated position.

The testing device 1, as shown in FIG. 1, consists of a container or inner cup 2 and an outer cup 3. The container 2 is provided with a constricted bottom part 4, over which the wall of the outer cup 3 can be moved, until the two parts 2, 3 are axially connected with each other by snap means 9, 10. These snap means consist of a central opening 9 arranged in the bottom 5 of the container 2 and a push or snap head 10 engaging in the central opening 9, which push or snap head 10 is arranged on the bottom 12 of the outer cup 3. The outer cup 3 is rotatable relatively to the container 2, as indicated by the arrow F in FIG. 3.

Figure 4:
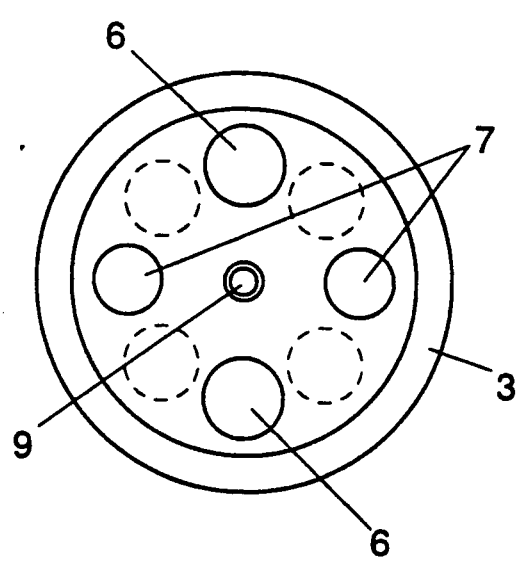
FIG. 4 is a bottom view of the container shown in FIG. 2.

The bottom 5 of the container 2 comprises two liquid passages 6, with an exactly determined amount of reagent 7 being applied to two places in the plane of the bottom 5 facing the outer cup 3, e.g., by a freeze-drying process. The surface of the reagent 7 may not extend beyond the lower surface of the bottom 5. As shown in FIG. 4, the reagent 7 is in a circumferentially shifted position relative to the liquid passages 6.

The bottom 12 of the outer cup 3 comprises two separate, diametrically opposed reservoirs 8, the contents of which are closely determined and attuned to the amount of reagent 7 contained in the bottom 5 of the container 2. It will be clear that in mounted condition, i.e. when the snap means 9, 10 engage with each other, the bottom 12 of the outer cup 3 and the bottom 5 of the inner cup 2 must sealingly abut against each other. This sealing can be obtained, e.g., if, in unmounted condition, the bottom 12 of the outer cup 3 is given a somewhat convex shape so that when the snap means 9, 10 are interconnected the bottom 12 comes to rest flatly on the bottom 5 of the inner cup 2. In order to obtain a proper sealing, the bottom 12 of the inner cup 3 can also be provided with a suitable sealing layer.

For observing a color change the bottom of the container 2 can be provided with sight glasses in those places where the reagent 7 is applied. The bottoms of the reservoirs 8 can also be sight glasses. Preferably, the outer cup 3 is made entirely of a transparent synthetic material.

With a view to easy rotatability of the container 2 and the outer cup 3 relative to each other, the outer faces of the parts 2, 3 are provided with vertical serrated edges.

Instead of two reservoirs 8, only one reservoir 8 may also be provided in the outer cup 3 while in the bottom 5 of the container 2 a reagent 7 may be applied in three places which are circumferentially spaced $\frac{1}{3} \pi$ radians. The contents of the reservoir 8 can then be successively contacted with the three reagents.

The embodiment shown in FIGS. 1–4 is rotationally symmetric in relation to the center line 11 of the container 2. It is also possible to give the container 2 a rectangular cross-section, in which case the outer cup 3 also has a rectangular cross-section, and which outer cup can be shifted relatively to the container 2 in a direction perpendicular to the center line 11 of the container 2. In the latter case the reservoirs 8 arranged in the outer cup 3 communicate with the interior of the container 2 in one end position, while in the other, shifted, end position the reservoir 8 enters in contact with the reagent 7 applied in the bottom 5 of the container 2.

The testing device is delivered to the user as a ready-made instrument, in which the outer cup 3 is put in such a position that the reservoirs thereof are opposite the places where the reagents 7 are applied. After filling the container 2, the outer cup 3 is shifted one quarter turn so that the reservoirs 8 receive an exact amount of, e.g., fresh milk. After rotating the outer cup 3 in the opposite direction, the reservoir 8 comes to lie opposite the reagent 7. The testing device is then turned through 180° and placed with the upper edge of the container 2 on a supporting surface. After some time a color change, if any, of the milk sample in the reservoir 8 can be observed through the transparent outer cup 3. The liquid testing device is suitable for single use and can be thrown away after use.

I claim:

1. A disposable liquid testing device consisting essentially of a container having a side wall and a bottom wall on a lower end of said side wall, and an outer cup having a side wall and a bottom wall on a lower end of said cup side wall sealingly placed and axially fixed on the lower end of the side wall, said outer cup being rotatable such that said outer cup can be put in at least two coplanar end positions relative to the container, the bottom wall of the container is provided with at least one liquid passage therethrough and at least one reagent is applied on a lower surface of said bottom wall facing the outer cup, and the bottom wall of the outer cup abuts against the bottom wall of the container and comprises at least one reservoir which is in the register with the liquid passage in one end position of the outer cup and in register with the reagent in the other end position.

2. A device as claimed in claim 1, characterized in that the outer cup and the container include snap means for connecting with each other.

3. A device as claimed in claim 2, characterized in that the bottom of the outer cup is deformable and is convex such that the bottom of the outer cup sealingly abuts against the bottom of the container.

4. A device as claimed in claim 3, characterized in that the bottom of the outer cup is provided with a sealing layer for sealing engagement against the bottom of the container.

5. A device as claimed in claim 4, characterized in that the outer cup is made of a transparent synthetic material.

6. A device as claimed in claim 3, characterized in that the outer cup is made of a transparent synthetic material.

7. A device as claimed in claim 2, characterized in that the bottom of the outer cup is provided with a sealing layer for sealing engagement against the bottom of the container.

8. A device as claimed in claim 7, characterized in that the outer cup is made of a transparent synthetic material.

9. A device as claimed in claim 2, characterized in that the outer cup is made of a transparent synthetic material.

10. A device as claimed in claim 1, characterized in that the bottom of the outer cup is deformable and is convex such that the bottom of the outer cup sealingly abuts against the bottom of the container.

11. A device as claimed in claim 10, characterized in that the bottom of the outer cup is provided with a sealing layer for sealing engagement against the bottom of the container.

12. A device as claimed in claim 11, characterized in that the outer cup is made of a transparent synthetic material.

13. A device as claimed in claim 10, characterized in that the outer cup is made of a transparent synthetic material.

14. A device as claimed in claim 1, characterized in that the bottom of the outer cup is provided with a sealing layer for sealing engagement against the bottom of the container.

15. A device as claimed in claim 14, characterized in that the outer cup is made of a transparent synthetic material.

16. A device as claimed in claim 1, characterized in that the outer cup is made of a transparent synthetic material.

* * * * *